(12) United States Patent
Weiss (10) Patent No.: US 8,343,914 B2
(45) Date of Patent: Jan. 1, 2013

(54) FIBRILLATION RESISTANT PROTEINS

(75) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 736 days.

(21) Appl. No.: 12/160,187

(22) PCT Filed: Jan. 8, 2007

(86) PCT No.: PCT/US2007/000320
§ 371 (c)(1), (2), (4) Date: Jun. 2, 2009

(87) PCT Pub. No.: WO2007/081824
PCT Pub. Date: Jul. 19, 2007

(65) Prior Publication Data
US 2009/0304814 A1    Dec. 10, 2009

Related U.S. Application Data

(60) Provisional application No. 60/756,930, filed on Jan. 6, 2006, provisional application No. 60/757,364, filed on Jan. 9, 2006.

(51) Int. Cl.
*A61K 38/28* (2006.01)
*C07K 14/62* (2006.01)
*C12N 15/00* (2006.01)

(52) U.S. Cl. ............ 514/6.2; 514/6.3; 514/6.4; 530/303; 530/304; 435/69.1

(58) Field of Classification Search .................. None
See application file for complete search history.

(56) References Cited

U.S. PATENT DOCUMENTS

| 5,149,716 | A | 9/1992 | Vertesy et al. |
| 5,149,777 | A | 9/1992 | Hansen et al. |
| 5,491,216 | A | 2/1996 | Hoffmann et al. |
| 5,506,202 | A | 4/1996 | Vertesy et al. |

(Continued)

FOREIGN PATENT DOCUMENTS
EP     1 090 640 A2    4/2001
(Continued)

OTHER PUBLICATIONS

Wan et al. Biochemistry 43: 16119-16133, 2004.*

(Continued)

*Primary Examiner* — Christine J Saoud
(74) *Attorney, Agent, or Firm* — Hahn Loeser & Parks LLP; John J. Cunniff (57) ABSTRACT

Protection of proteins against fibrillation may be afforded by introduction of certain histidine substitutions into the protein, such that a pair of histidines are present with sufficient spacing as to allow the histidines to coordinate with zinc. In the case of insulin, introduction of histidine residue substitutions at residues A4 and A8 together or a histidine residue substitution at residue B1, provides increased resistance to fibrillation while maintaining at least a majority of the activity of the insulin analogue. Introduction of a histidine residue substitution at residue A8 restores at least a portion of fibrillation resistance that may have been harmed by substitutions present on the B-chain such as those present in fast-acting insulins. Proteins protected by such histidine substitutions may be used to provide a pharmaceutical composition. A method of treating a patient includes administering a physiologically effective amount of the pharmaceutical composition to the patient.

19 Claims, 6 Drawing Sheets

U.S. PATENT DOCUMENTS

| | | | |
|---|---|---|---|
| 5,618,913 | A | 4/1997 | Brange et al. |
| 5,698,669 | A | 12/1997 | Hoffmann et al. |
| 5,700,662 | A | 12/1997 | Chance et al. |
| 5,716,927 | A | 2/1998 | Balschmidt et al. |
| 5,977,297 | A | 11/1999 | Obermeier et al. |
| 6,011,007 | A | 1/2000 | Havelund et al. |
| 6,221,633 | B1 | 4/2001 | Ertl et al. |
| 6,268,335 | B1 | 7/2001 | Brader |
| 6,465,426 | B2 | 10/2002 | Brader |
| 6,531,448 | B1 | 3/2003 | Brader |
| 6,630,348 | B1 | 10/2003 | Lee et al. |
| 7,129,211 | B2 | 10/2006 | Bhattacharya et al. |
| 7,316,999 | B2 | 1/2008 | Hoeg-Jensen et al. |
| 7,547,821 | B2 | 6/2009 | Moloney et al. |
| 2001/0036916 | A1 | 11/2001 | Brader |
| 2002/0082199 | A1 | 6/2002 | Brader |
| 2003/0104981 | A1 | 6/2003 | Mandic |
| 2003/0144181 | A1 | 7/2003 | Brader |
| 2004/0014660 | A1 | 1/2004 | During et al. |
| 2004/0053816 | A1 | 3/2004 | Bhattacharya et al. |
| 2004/0214988 | A1 | 10/2004 | Tirrell et al. |
| 2005/0014679 | A1 | 1/2005 | Beals et al. |
| 2005/0039235 | A1 | 2/2005 | Moloney et al. |
| 2005/0176621 | A1 | 8/2005 | Brader et al. |
| 2006/0217290 | A1 | 9/2006 | Kohn et al. |
| 2007/0129284 | A1 | 6/2007 | Kjeldsen et al. |
| 2008/0146492 | A1 | 6/2008 | Zimmerman et al. |
| 2010/0099601 | A1 | 4/2010 | Weiss |
| 2011/0059887 | A1 | 3/2011 | Weiss |
| 2011/0077196 | A1 | 3/2011 | Weiss |
| 2011/0077197 | A1 | 3/2011 | Habermann et al. |
| 2011/0166064 | A1 | 7/2011 | Weiss |
| 2011/0195896 | A1 | 8/2011 | Weiss et al. |

FOREIGN PATENT DOCUMENTS

| | | |
|---|---|---|
| WO | 03/053339 A2 | 7/2003 |
| WO | 2005/054291 A1 | 6/2005 |
| WO | 2007/081824 A2 | 7/2007 |
| WO | 2007/096332 A1 | 8/2007 |
| WO | 2007/081824 A3 | 2/2008 |
| WO | 2008/043033 A2 | 4/2008 |
| WO | 2008/043033 A3 | 11/2008 |
| WO | 2009/087081 A2 | 7/2009 |
| WO | 2009/129250 A2 | 10/2009 |
| WO | 2009/132129 A2 | 10/2009 |
| WO | 2010/132129 A3 | 1/2010 |
| WO | 2009/129250 A3 | 2/2010 |
| WO | 2010/014946 A2 | 2/2010 |
| WO | 2010/014946 A3 | 5/2010 |
| WO | 2011/028813 A2 | 3/2011 |
| WO | 2011/072288 A2 | 6/2011 |

OTHER PUBLICATIONS

EP 07 84 3856 Supplementary European Search Report, 4 pages; Dec. 11, 2009.

Currie et al.; The influence of glucose—lowering therapies on cancer risk in type 2 diabetes; Diabetologia; 52(9); pp. 1766-1777; Sep. 2009.

Hemkens et al.; Risk of malignancies in patients with diabetes treated with human insulin or insulin analogues: a cohort study; Diabetologia 52(9); pp. 1732-1744; Sep. 2009.

Tuffs; German agency suspects that insulin analogue glargine increases risk of cancer; PubMed; BMJ; 339:b2774; 1 page (no abstract available); Jul. 8, 2009.

Shukla et al.; Analysis of signaling pathways related to cell proliferation stimulated by insulin analogs in human mammary epithelial cell lines; Endrocine-Related Cancer; 16(2); pp. 429-441; Jun. 2009.

Rajpal et al.; Single-Chain Insulins as Receptor Agonists; The Endrocrine Society; 27 pages; Feb. 19, 2009.

Weinstein, et al.; Insulin analogues display IGF-I-like mitogenic and anti-apoptotic activities in cultured cancer cells; Diabetes/Metabolism Research and Reviews; 25(1); pp. 41-49; Jan. 2009.

Zelobowska et al.; Mitogenic potency of insulin glargine; Polish Journal of Endocrinology; vol. 60, No. 1; pp. 34-39; 2009.

Hua et al.; Design of an Active Ultrastable Single-chain Insulin Analog; The Journal of Biological Chemistry; vol. 283, No. 21; pp. 14703-14716; May 23, 2008.

Liefvendahl et al.; Mitogenic effect of the insulin analogue glargine in malignant cells in comparison with insulin and IGF-I; PubMed; 1 page (abstract only); Apr. 7, 2008.

Du et al.; Insulin analogs with B24 or B25 phenylalanine replaced by biphenylalanine; Acta Biochem Biophys Sin; vol. 40, No. 2; pp. 133-139; Feb. 2008.

Mayer et al.; Proliferative effects of insulin analogues on mammary epithelial cells; Archives of Physiology and Biochemistry; 114(1); pp. 38-44; Feb. 2008.

Kohn et al.; pI-shifted insulin analogs with extended in vivo time action and favorable receptor selectivity; PubMed; 28 (4); 1 page (abstract only); Jan. 25, 2007.

Nakagawa, et al.; Chiral Mutagenesis of Insulin; The Journal of Biological Chemistry; vol. 281, No. 31; pp. 22386-22396; Aug. 4, 2006.

Hua et al.; Mechanism of insulin fibrillation—The structure of insulin under amyloidogenic conditions resembles a protein—folding intermediate, Journal of Biological Chemistry; vol. 279, No. 20; pp. 21449-21460, XP002557730, ISSN 0021-9258; May 14, 2004.

Chen et al.; Sequences of B-Chain/Domain 1-10/1-9 of Insulin and Insulin-like Growth Factor 1 Determine Their Different Folding Behavior; Biochemistry; pp. 9225-9233; 2004.

Zakova et al.; Shortened Insulin Analyogues: Marked Changes in Biological Activity Resulting from Replacement of TyrB26 and N-Methylation of Piptide Bonds in the C-Terminus of the B-Chain; Biochemistry; vol. 43; pp. 2323-2331; 2004.

Garriques et al.; The effect of mutations on the structure of insulin fibrils studied by Fourier transform infrared (FTIR) spectroscopy and electron microscopy; PubMed; vol. 12; 1 page (abstract only); 2002.

Weiss, et al.; Activities of Monomeric Insulin Analogs at Position A8 Are Uncorrelated with Their Thermodynamic Stabilities; The Journal of Biological Chemistry; vol. 276, No. 43; pp. 40018-40024; Oct. 26, 2001.

Nielsen et al.; Probing the Mechanism of Insulin Fibril Formation with Insulin Mutants; American Chemical Society; Biochemistry; vol. 40; pp. 8397-8409; Jun. 19, 2001.

Milazzo et al.; ASPB10 insulin induction of increased mitogenic responses and phenotypic changes in human breast epithelial cells; evidence for enhanced interations with the insulin-like growth factor-I receptor; PubMed; 18(1); 1 page (abstract only); Jan. 1997.

Doig et al.; N- and C-capping preferences for all 20 amino acids in {alpha}—helical peptides; Protein Science; vol. 4; pp. 1325-1335; 1995.

Mirmira et al.; Role of the Phenylalanine B24 Side Chain in Directing Insulin Interaction with Its Receptor; The Journal of Biological Chemistry; vol. 264, No. 11; pp. 6349-6354; Apr. 15, 1989.

Kristensen, Claus et al.; Alanine Scanning Mutagenesis of Insulin; The Journal of Biological Chemistry; May 16, 1997; pp. 12978-12983; vol. 272, No. 20; U.S.A.

Weiss, Michael A. et al.; Non-standard Insulin Design: Structure-Activity Relationships at the Periphery of the Insulin Receptor; Journal of Molecular Biology; Jan. 11, 2002, pp. 103-111; vol. 315, Issue 2.

Olsen, Helle B. et al.; The Relationship Between Insulin Bioactivity and Structure in the NH2—terminal A-chain Helix; Journal of Molecular Biology; Nov. 27, 1998, pp. 477-488; vol. 284, Issue 2.

Kaarsholm, Niels C. et al.; Engineering Stability of the Insulin Monomer Fold with Application to Structure—Activity Relationships; Biochemistry; Oct. 1993; pp. 10773-10778; 32 (40).

Zhao et al.; Design of an insulin analog with enhanced receptor binding selectivity: rationale, structure, and therapeutic implications; J. Biol. Chem. 284(46); Sep. 29, 2009; pp. 32178-32187.

Sreekanth et al.; Structural interpretation of reduced insulin activity as seen in the crystal structure of human Arg-insulin; Biochimie; 90(3); Sep. 22, 2007; pp. 467-473.

Kohn et al.; pI-shifted insulin analogs with extended in vivo time action and favorable receptor selectivity; Peptides; 28 (4); Jan. 25, 2007; pp. 935-948.

Sleiker et al.; Modifications in the B10 and B26-30 regions of the B chain of human insulin alter affinity for the human IGF-I receptor more than for the insulin receptor; Diabetologia; 40 Suppl. 2; Jul. 1997; pp. S54-S61.

Summ et al.; Binding of insulin analogs to partially purified insulin receptor from rat liver membrane (author's trans.); Hoppe Seylers Z. Physiol. Chem.; 357(5); May 1976; pp. 683-693 (Abstract only-1 page).

PCT/US2010/047546 International Search Report and Written Opinion dated May 23, 2011.

PCT/US2010/060085 International Search Report and Written Opinion dated Sep. 16, 2011.

PCT/US11/25730 International Search Report and Written Opinion dated Jul. 22, 2011.

EP 09 80 3678 Supplementary European Search Report dated Jan. 30, 2012.

Blanquart et al.; Characterization of IRA/IR hybrid insulin receptors using bioluminescence resonance energy transfer; Biochemical Pharmacology 76 (2008); Jul. 27, 2008, pp. 873-883.

Duckworth et al.; Degradation products of insulin generated by hepatocytes and by insulin protease; Journal of Biological Chemistry, vol. 263, No. 4, Apr. 6, 1988, pp. 1826-1833.

Haijuan Du et al.; Insulin analogs with B24 or B25 phenylalanine replaced by bipheylalanine; ACTA Biochimica et Biophysica Sinica, vol. 40, No. 2, 2006, pp. 133-139.

Huang et al,; Structure-Specific Effects of Protein on Cross $\beta$ Assembly: Studies of Insulin Fibrillation; Biochemistry 2006, 45, Aug. 4, 2006, pp. 10278-10293.

Liu et al.; Utilization of combined chemical modification to enhance the blood-brain barrier permeability and pharmacological activity of endomorphin-a, JPET 106, 106484, Jun. 27, 2006, pp. 1-43.

Mirmira et al.; Disposition of the phenylalanine B25 side chain during insulin-receptor and insulin-insulin interactions, Biochemistry; vol. 30, No. 33; May 1, 1991, pp. 8222-8229.

Mirmira et al.; Importance of the character and configuration of residues B24 B25 and B26 in insulin-receptor interactions, Journal of Biological Chemistry, vol. 266, No. 3; Jan. 25, 1991, pp. 1428-1436.

Stemaszynska et al.; N-(2-Oxoacyl)amino Acids and Nitriles as Final Products of Dipeptide Chlorination Mediated by the Myeloperoxidase/H202/CI-System, European Journal of Biochemistry, vol. 92, No. 1, Sep. 25, 1978, pp. 301-308.

Yang et al.; An Achilles' heel in an amyloidogenic protein and its repair: insulin fibrillation and therapeutic design; J Biol Chem. Apr. 2, 2010:285(14):10806-21.

* cited by examiner

FIG. 1A
(PRIOR ART)
PROINSULIN

FIG. 1B
(PRIOR ART)
MODEL

FIBRILLATION RESISTANT PROTEINS

CROSS REFERENCE TO RELATED APPLICATIONS

This application claims priority from U.S. Provisional Patent Application Nos. 60/756,930 and 60/757,364 filed on Jan. 6, 2006 and Jan. 9, 2006, respectively.

STATEMENT REGARDING FEDERALLY SPONSORED RESEARCH OR DEVELOPMENT

This invention was made with government support under cooperative agreements awarded by the National Institutes of Health, Contract No. NIH RO1DK069764. The U.S. government may have certain rights to the invention.

BACKGROUND OF THE INVENTION

The stability of proteins used in medical treatment is an important concern in medicine. Protein degradation can be classified as physical or chemical degradation. Chemical degradation of proteins can include deamination or transamination of the protein. Physical degradation may include a change in conformation that leads to aggregation of the protein and formation of protein fibrils. The present invention concerns the prevention of fibrillation.

Figure 1A:
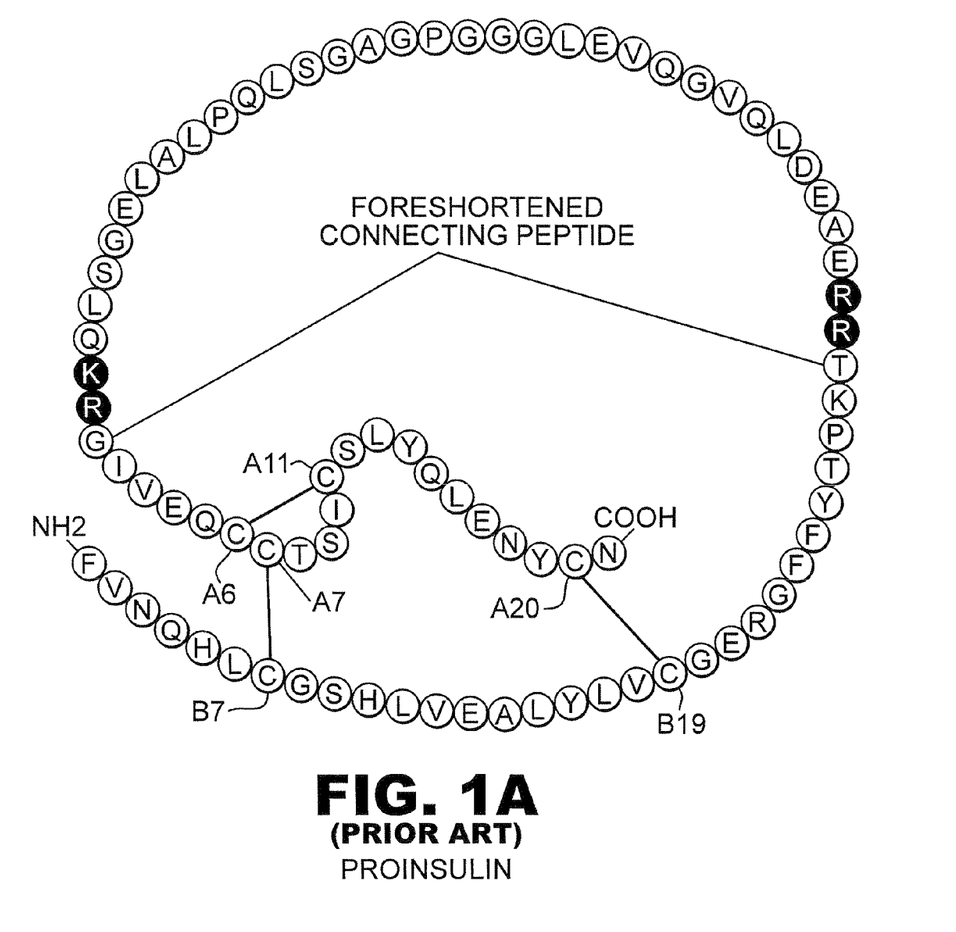
FIG. 1A is a schematic representation of the sequence of human proinsulin (SEQ ID NO: 11) including the A and B chains and the connecting region shown with flanking dibasic cleavage sites (filled circles) and C-peptide (open circles). The line labeled "foreshortened connecting peptide" represents the connecting region in mini-proinsulin, which is a proinsulin analogue containing a dipeptide (Ala-Lys) linker between the A chain and B chain portions of insulin.
Figure 1B:
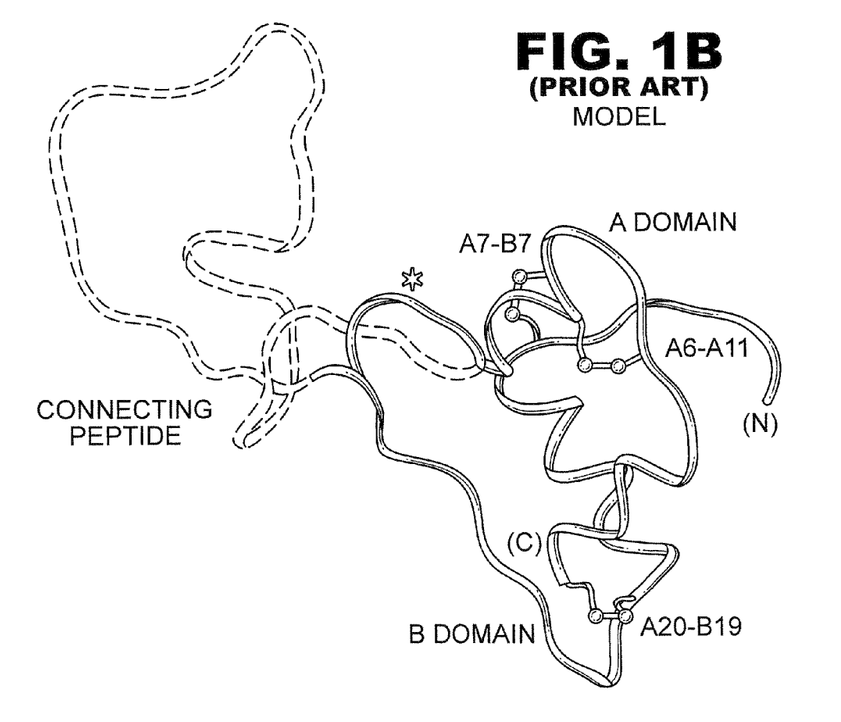
FIG. 1B provides a structural model of proinsulin, consisting of an insulin-like moiety and disordered connecting peptide (dashed line). The asterisk indicates the location of a foreshortened AK linker in mini-proinsulin.
Figure 2:
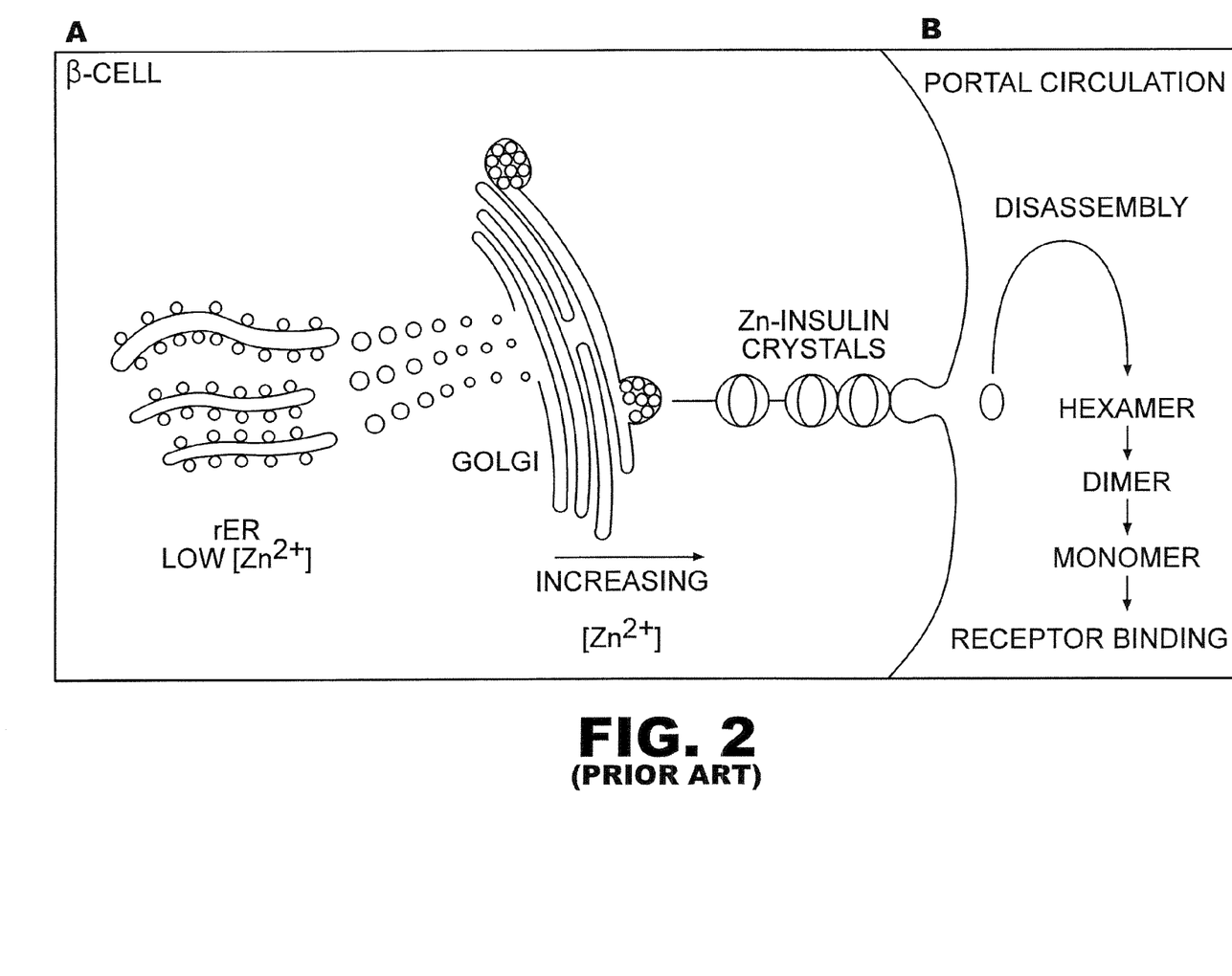

Administration of the protein insulin has long been established as a treatment for diabetes. Insulin is a small globular protein that plays a central role in metabolism in vertebrates. Insulin contains two chains, an A chain, containing 21 residues and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). Although the structure of proinsulin has not been determined, a variety of evidence indicates that it consists of an insulin-like core and disordered connecting peptide (FIG. 1B). Formation of three specific disulfide bridges (A6-A11, A7-B7, and A20-B19; FIG. 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). Assembly and disassembly of native oligomers is thus intrinsic to the pathway of insulin biosynthesis, storage, secretion, and action (FIG. 2).

Figure 1C:
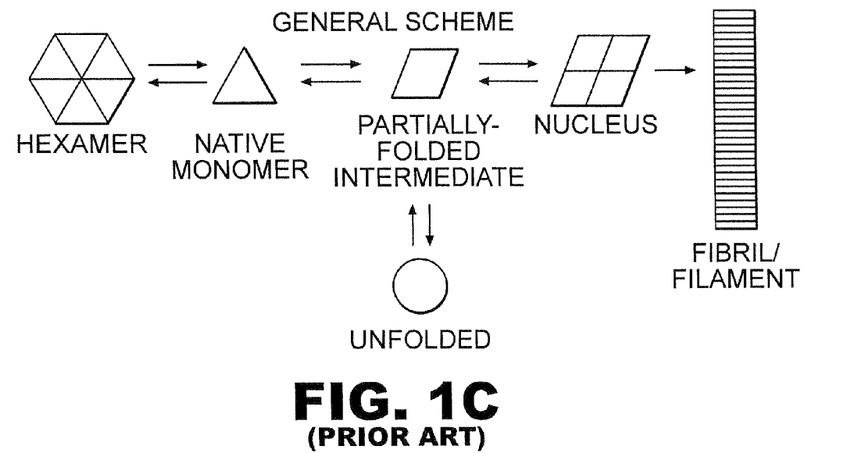

Insulin readily misfolds in vitro to form a prototypical amyloid. Unrelated to native assembly, fibrillation is believed to occur via an amyloidogenic partial fold (FIG. 1C). Factors that accelerate or hinder fibrillation have been extensively investigated in relation to pharmaceutical formulations. Zinc-free insulin is susceptible to fibrillation under a broad range of conditions and is promoted by factors that impair native dimerization and higher order self-assembly. It is believed that the structure of active insulin is stabilized by axial zinc ions coordinated by the side chains of $His^{B10}$.

Amino-acid substitutions in the A- and/or B-chains of insulin have widely been investigated for possible favorable effects on the pharmacokinetics of insulin action following subcutaneous injection. Examples are known in the art of substitutions that accelerate or delay the time course of absorption. Such substitutions (such as $Asp^{B28}$ in the insulin analogue sold under the trademark NOVALOG® and [$Lys^{B28}$, $Pro^{B29}$] in the insulin analogue sold under the trademark HUMALOG®) can be and often are associated with more rapid fibrillation and poorer physical stability. Indeed, a series of ten analogs of human insulin for susceptibility to fibrillation, including $Asp^{B28}$-insulin and $Asp^{B10}$-insulin have been tested. All ten were found to be more susceptible to fibrillation at pH 7.4 and 37° C. than is human insulin. The ten substitutions were located at diverse sites in the insulin molecule and are likely to be associated with a wide variation of changes in classical thermodynamic stability. These results suggest that substitutions that protect an insulin analogue from fibrillation under pharmaceutical conditions are rare; no structural criteria or rules are apparent for their design.

Fibrillation, which is a serious concern in the manufacture, storage and use of insulin and insulin analogues for diabetes treatment, is enhanced with higher temperature, lower pH, stifling or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, diabetic individuals optimally must keep insulin refrigerated prior to use. Fibrillation of insulin or insulin analogue can be a particular concern for diabetic patients utilizing an insulin pump, in which small amounts of insulin or insulin analogue are injected into the patient's body at regular intervals. In such a usage, the insulin or insulin analogue is not kept refrigerated within the pump apparatus and fibrillation of insulin can result in blockage of the catheter used to inject insulin or insulin analogue into the body, potentially resulting in unpredictable blood glucose level fluctuations or even dangerous hyperglycemia. At least one recent report has indicated that lispro insulin (an analogue in which residues B28 and B29 are interchanged relative to their positions in wild-type human insulin; the product sold under the trademark HUMALOG®) may be particularly susceptible to fibrillation and resulting obstruction of insulin pump catheters.

Insulin fibrillation is an even greater concern in implantable insulin pumps, where the insulin would be contained within the implant for 1-3 months at high concentration and at physiological temperature (i.e. 37° C.), rather than at ambient temperature as with an external pump. Additionally, the agitation caused by normal movement would also tend to accelerate fibrillation of insulin. In spite of the increased potential for insulin fibrillation, implantable insulin pumps are still the subject of research efforts, due to the potential advantages of such systems. These advantages include intraperitoneal delivery of insulin to the portal circulatory system, which mimics normal physiological delivery of insulin more closely than subcutaneous injection, which provides insulin to the patient via the systemic circulatory system. Intraperitoneal delivery provides more rapid and consistent absorption of insulin compared to subcutaneous injection, which can provide variable absorption and degradation from one injection site to another. Administration of insulin via an implantable pump also potentially provides increased patient convenience. Whereas efforts to prevent fibrillation, such as by addition of a surfactant to the reservoir, have provided some improvement, these improvements have heretofore been considered insufficient to allow reliable usage of an implanted insulin pump in diabetic patients outside of strictly monitored clinical trials.

Resistance to fibrillation caused by heat or other causes would be advantageous not only for insulin and insulin analogs, but for a variety of medically useful proteins, especially in tropical and sub-tropical regions of the developing world. The major barrier to the storage and practical use of presently available pharmaceutical formulations of insulin and insulin analogues at temperatures above 30° C. is due to accelerated fibrillation of the protein. The major reason for limitations to the shelf life of presently available pharmaceutical formulations of insulin and insulin analogues at temperatures above 10° C. is due to fibrillation of the protein. Fibrillation is of special concern for fast-acting or "mealtime" insulin analogues (such as the products sold under the trademarks HUMALOG® and NOVALOG®) when these formulations are diluted by the patient and stored at room temperature for more than 15 days.

Modifications of proteins such as insulin are known to increase resistance to fibrillation but impair biological activity. For example, "mini-proinsulin," a proinsulin analogue containing a dipeptide linker between the A and B chains of insulin, is resistant to fibrillation but is impaired in its activity. Therefore, a need exists for insulin analogues and other protein analogues that are resistant to fibrillation and that maintain at least a majority of their biological activity.

SUMMARY OF THE INVENTION

It is, therefore, an aspect of the present invention to provide protein analogues that are more resistant to fibrillation than their wild-type counterparts, while maintaining biological activity.

It is another aspect of the present invention to provide insulin analogues that are more resistant to fibrillation than their counterpart insulins but maintain at least a majority of their biological activity.

It is still another aspect of the present invention to provide an insulin A- or B chain analogue that, as a part of an insulin analogue, provides increased resistance to fibrillation compared to the non-analogue counterpart insulin.

It is still another aspect of the present invention to provide amino-acid substitutions in the insulin A- or B chains such that, as a part of an unrelated insulin analogue with enhanced susceptibility to fibrillation, the substitutions described herein at least partially compensate for the instability of the original analogue to provide increased resistance to fibrillation relative to non-substituted counterpart analogue.

It is yet another aspect of the present invention to provide a nucleic acid that encodes for at least a portion of an insulin analogue that displays increased resistance to fibrillation compared to a non-analogue insulin.

In general, the present invention provides a vertebrate insulin analogue or a physiologically acceptable salt thereof, comprising at least one of the following substitutions: histidine residue substitutions at residues A4 and A8 together, and a histidine residue substitution at residue B1. In one example, the vertebrate insulin analogue is a mammalian insulin analogue, such as a human, porcine, bovine or equine insulin analogue. The histidine substitutions specified above may be used in combination with each other (A4, A8 and B1 tri-substitutions); the B1 or paired A4-A8 histidine substitutions may also be combined with unrelated substitutions elsewhere in the insulin molecule intended to introduce other favorable pharmaceutical properties unrelated to resistance to fibrillation.

Additionally, in some embodiments, the present invention provides an insulin analogue with an increased resistance to fibrillation over its counterpart analogues. Known insulin analogs (such as the products sold under the trademarks HUMALOG® and NOVALOG®) have an increased susceptibility to fibrillation. The present invention also specifies the use of histidine (i) singly at position B1, (ii) singly at position A8, (iii) at A8 in combination with histidine also at A4, or (iv) jointly at positions B1, A4, and A8 to compensate for the instability of insulin analogues containing amino-acid substitutions in the B-chain (such as but not restricted to substitutions at position B28 and/or position B29) for the purpose of augmenting their resistance to fibrillation.

The present invention likewise provides a pharmaceutical composition comprising such insulin analogues and which may additionally include zinc ions. Optimally, in the presence of phosphate-containing buffers, zinc ions may be included in such a composition at a level of a molar ratio of between 2.2 and 3.0 per hexamer of the insulin analogue; in the presence of buffers based on Tris Hydroxymethylaminoethane (Tris), or other buffers that, like Tris, do not bind well to zinc ions to form an insoluble salt, zinc ions may be included in such a composition at a level of a molar ratio of between 2.2 and 5.0 per hexamer of the insulin analogue. In such a formulation the concentration of the insulin analogue would typically be between 0.1 and 1.5 mM. Excipients may include glycerol, glycine, other buffers and salts, and anti-microbial preservatives such as phenol and meta-cresol; the latter preservatives are known to enhance the stability of the insulin hexamer. Such a pharmaceutical composition may be used to treat a patient having diabetes or other medical condition by administering a physiologically effective amount of the composition to the patient.

The present invention also provides a nucleic acid comprising a sequence that encodes a polypeptide selected from the group consisting of an A chain insulin analogue containing histidine residue substitutions at residues A4 and A8, a B chain insulin analogue containing a histidine residue substitution at residue B1, and combinations thereof. The nucleic acid sequence may encode either the isolated A- and B chain analogue, a modified A- or B chain containing an unrelated substitution or extension elsewhere in the polypeptide, modified proinsulin analogues, or single-chain insulin analogues containing a modified or foreshortened connecting domain. The nucleic acid may also be a portion of an expression vector, and that vector may be inserted into a host cell such as a prokaryotic host cell like an *E. coli* cell line, or a eukaryotic cell line such as as *S. cereviciae* or *Pischia Pastoris* strain or cell line.

The present invention likewise provides a method of increasing the resistance of polypeptides to fibrillation. The method includes introducing a histidine substitution or two paired histidine substitutions into the polypeptide such that a pair of histidine are present in the polypeptide with sufficient spacing between the pair of histidines as to allow the side chains of the histidines to coordinate with zinc. In one example, there are three intervening amino acids between the pair of histidines. In another example, the pair of histidines are present in an α-helix of the polypeptide. It is envisioned that the method would also work with a spacing of two intervening amino acids between the histidines. The method may be utilized to introduce one or more histidine substitutions into the A or B chain of a vertebrate insulin to increase the resistance of the resulting insulin to fibrillation. Irrespective of theory, the method may also utilize a histidine substitution in one chain of insulin to compensate for enhanced susceptibility to fibrillation caused by substitutions in the other chain. For example, Histidine substitutions at A8 alone or at A4 and A8 together may compensate for enhanced susceptibility to fibrillation caused by substitutions or other changes in the B-chain.

Chemical degradation of insulin, such as deamination, isopeptide bond formation, and disulfide interchange leading to formation of covalent polymers, is known to be reduced by formulations or modifications that enhance the thermodynamic stability of the native molecular structure of the insulin or insulin analogue. While not wishing to be bound by theory, introduction of a pair of histidine residues on the surface of a protein may confer a zinc-dependent increase in thermodynamic stability and so delay chemical degradation of the protein.

It is still another aspect of the present invention to provide a method treating a patient comprising administering a fibrillation-resistant insulin analogue to the patient. In one example, the fibrillation-resistant insulin analogue is a single-chain insulin analogue. In another example, the insulin is administered by an external or implantable insulin pump.

BRIEF DESCRIPTION OF THE SEVERAL VIEWS OF THE DRAWINGS

FIG. 1C provides a representation of a proposed pathway of insulin fibrillation via partial unfolding of monomer. The native state is protected by classic self-assembly (far left). Disassembly leads to equilibrium between native- and partially folded monomers (open triangle and trapezoid, respectively). This partial fold may unfold completely as an off-pathway event (open circle) or aggregate to form a nucleus en route to a protofilament (far right).

FIG. 2 is a representation of the pathway of insulin biosynthesis, storage, and secretion. A, nascent proinsulin folds as a monomer in ER wherein zinc-ion concentration is low; in Golgi apparatus zinc-stabilized proinsulin hexamer assembles, which is processed by cleavage of connecting peptide to yield mature insulin. Zinc-insulin crystals are observed in secretory granules. B, on metabolic stimulus, zinc-insulin crystals are released into portal circulation (pink) and disassociate in steps to liberate the functional monomer.

DETAILED DESCRIPTION OF THE INVENTION

The present invention is directed toward recombinant proteins that provide increased resistance to fibrillation. Particularly, the present invention provides insulin analogues that are resistant to fibrillation. To that end, the present invention provides insulin analogues that contain histidine (His) residue substitutions at positions A8, A4 and A8, or at B1. The insulin analogues of the present invention may include insulin analogues containing His substitutions at all three of the positions A4, A8, and B1. In one particular example, an insulin analogue of the present invention contains only a His substitution at position B1.

While not wishing to be bound by theory, it is believed that when the $His^{B1}$ substitution is present, the side chain of the B1 His residue, in combination with the B5 histidine side chain, provides a potential B1-B5 bi-histidine Zn-binding site, which confers Zn-dependent protection from fibrillation. Similarly, while not wishing to be bound by theory, it is believed that the [$His^{A4}$, $His^{A8}$] substitutions also provide a potential bi-histidine Zn-binding site, which confers protection from fibrillation. It is further envisioned that zinc stabilization of insulin will not affect activity in vivo because such zinc-protein structures are predicted to dissociate at protein and zinc concentrations less than about 1 μM. The protective effect of zinc binding may be mediated either though binding to the native molecular structure or to a distorted molecular structure as is thought to occur as an intermediate in the process of fibrillation.

Additionally, while not wishing to be bound by theory, it is believed that when the $His^{A8}$ substitution is present in the presence or absence of zinc and irrespective of histidines substitutions at B1 and/or A4, insulin analogues containing otherwise fibrillation-enhancing amino acid substitutions in the B-chain will regain at least some resistance to fibrillation compared to the corresponding insulin analogue containing only the fibrillation enhancing B-chain substitution or substitutions.

As used in this specification and the claims, various analogues may be noted by the amino acid being substituted, followed by the position of the amino acid, optionally in superscript. The position of the amino acid in question includes the A or B chain of insulin where the substitution is located. Thus, $His^{B1}$ denotes a histidine substitution at the first amino acid of the B chain of insulin. $His^{A4}$ denotes a histidine substitution at the fourth amino acid of the A chain of insulin, and $His^{A8}$ denotes a histidine substitution at the eighth amino acid of the A chain of insulin. Unless noted otherwise or wherever obvious from the context, the amino acids noted herein should be considered to be L-amino acids.

It is envisioned that the substitutions of the present invention may be made in any of a number of existing insulin analogues. For example, the $His^{A8}$, [$His^{A4}$, $His^{A8}$], or $His^{B1}$ substitutions, or combinations thereof, may be made in insulin analogues such as Lispro insulin (sold under the trademark HUMALOG®), insulin Aspart (sold under the trademark NOVALOG®), other modified insulins or insulin analogues, or within various pharmaceutical formulations, such as regular insulin, NPH insulin, lente insulin or ultralente insulin, in addition to human insulin. These substitutions may also be introduced into analogues of human insulin that, while not clinically used, are still useful experimentally, such as DKP-insulin, which contains the substitutions $Asp^{B10}$ (D), $Lys^{B28}$ (K) and $Pro^{B29}$ (P), or miniproinsulin, a proinsulin analogue containing a dipeptide (Ala-Lys) linker between the A chain and B chain portions of insulin in place of the normal 35 amino acid connecting region between the C-terminal residue of the B chain and the N-terminal residue of the A chain.

The present invention is not limited to human insulin and its analogues however. It is also envisioned that these substitutions may also be made in animal insulins such as porcine, bovine, equine, and canine insulins, by way of non-limiting examples.

Furthermore, in view of the similarity between human and animal insulins, and use in the past of animal insulins in human diabetic patients, it is also envisioned that other minor modifications in the sequence of insulin may be introduced, especially those substitutions considered "conservative" substitutions. For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M) Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). In one example, the insulin analogue of the present invention contains three or fewer conservative substitutions other than the [$His^{A4}$, $His^{A8}$], or His substitutions of the present invention. In another example, the insulin analogue of the present invention contains one or fewer conservative substitutions other than the $His^{A8}$, [$His^{A4}$, $His^{A8}$], or $His^{B1}$ substitutions of the present invention.

The amino-acid sequence of the A chain of human insulin is provided, for comparative purposes, as SEQ ID NO: 1. The amino acid sequence of an analogue of the A chain of human insulin containing the $His^{A4}$ and $His^{A8}$ substitutions is provided as SEQ ID NO: 2. The amino acid sequence of the B chain of human insulin is provided, for comparative purposes, as SEQ ID NO: 3. The amino acid sequence of an analogue of the B chain of human insulin containing the His substitution is provided as SEQ ID NO: 4. Further combinations of other substitutions are also within the scope of the present invention. It is also envisioned that the substitutions of the present invention may also be combined with substitutions of prior known insulin analogues. For example, the amino acid sequence of an analogue of the B chain of human insulin containing the $Lys^{B28}$ $Pro^{B29}$ substitutions of lispro insulin combined with the $His^{B1}$ substitution is provided as SEQ ID NO: 5. Likewise, the amino acid sequence of an analogue of the B chain of human insulin containing the $Asp^{B28}$ substitution of aspart insulin, combined with the $His^{B1}$ substitutions, is provided as SEQ ID NO: 6.

By way of example and not of limitation, it is also envisioned that the [$His^{A4}$, $His^{A8}$], and/or $His^{B1}$ substitutions of the present invention may also be made in an insulin analogue or proinsulin analogue having the amino acid sequence represented by formula I (SEQ ID NO: 11), (I)
R1-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-R2-R3-Thr-Xaa$_{0-35}$-Gly-Ile-Val-R4-Gln- Cys-Cys-R5-Ser-Ile-Cys-Ser-Leu-Tyr-Gln-Leu-Glu- Asn-Tyr-Cys-Asn;

wherein R1 is His or Phe; wherein R2 is Pro, Lys, or Asp; wherein R3 is Lys or Pro; wherein R4 is His or Glu; wherein R5 is His or Thr; and wherein Xaa$_{0-35}$ is 0-35 of any amino acid or a break in the amino acid chain;

and further wherein at least one substitution selected from the group of the following amino acid substitutions is present:
R1 is His; and
R5 is His; and
R4 and R5 together are His.

Analogues of insulin containing the $His^{B1}$, $His^{A8}$, or the [$His^{A4}$, $His^{A8}$] substitutions were made in human insulin and DKP insulin as follows. The tetra-S-sulfonate derivative of the A chain was obtained by oxidative sulfitolysis of human insulin (provided by Eli Lilly and Co., Indianapolis, Ind.) followed by separation of the S-sulphonated A and B chains as known in the art. A and B-chain analogues were prepared by solid-phase chemical synthesis. 4-methylbenzhydrylamine resin (0.6 mmol of amine/g; Bachem, Inc.) was used as solid support for synthesis of A-chain analogues; (N-tert-butoxycarbonyl, O-benzyl)-threonine-PAM resin (0.56 mmol/g; Bachem, Inc.) was used as solid support for synthesis of B-chain analogues. A manual double-coupling protocol was followed. Insulin analogues were prepared by chain combination in 0.1M glycine buffer (pH 10.6) in the presence of 4.5 mM dithiothreitol (DTT). Analogues were purified by size exclusion chromatography (Bio-Gel P-4 in 3M acetic acid) and preparative reverse phase HPLC Predicted molecular masses were confirmed by matrix-assisted laser desorption ionization (MALDI-TOF) mass spectrometry (MS).

The following analogues were synthesized and tested for activity and resistance to fibrillation as provided herein in comparison to human insulin and otherwise unmodified DKP-insulin. An A-chain analogue having the sequence of SEQ ID NO: 2 was combined with a B chain peptide having the sequence of SEQ ID NO: 3 to provide a [$His^{A4}$, $His^{A8}$]-insulin analogue. A [$His^{A4}$, $His^{A8}$]-DKP-insulin analogue was prepared with the peptides identified by SEQ ID NOS: 2 and 7. A $His^{B1}$-insulin analogue was prepared with peptides having the sequences of SEQ ID NOS: 1 and 4. A $His^{B1}$-DKP-insulin analogue was prepared with the peptides identified by SEQ ID NOS: 1 and 8. A $His^{A8}$-DKP-insulin analogue was prepared with the peptides identified by SEQ ID NOS: 9 and 7. The rationale of testing of substitutions in the context of a monomeric analog is that the insulin monomer is thought to be an obligatory intermediate in the molecular pathway of fibrillation; protective effects in the context of a zinc insulin hexamer would be expected to be similar or greater. In addition, the crystal structure of an insulin analogue containing the paired substitutions [$His^{A4}$, $His^{A8}$] was determined in the presence of zinc ions to verify the formation of a novel zinc-ion-binding site involving the introduced histidines side chains at these positions.

Receptor-Binding Assays.

Relative activity is defined as the ratio of analogue to wild-type human insulin required to displace 50 percent of specifically bound $^{125}$I-human insulin. A human placental membrane preparation containing the insulin receptor (IR) was employed as known in the art. Membrane fragments (0.025 mg protein/tube) were incubated with $^{125}$I-labeled insulin (ca. 30,000 cpm) in the presence of selected concentrations of unlabelled analogue for 18 hours at 4° C. in a final volume of 0.25 ml of 0.05 M Tris-HCl and 0.25 percent (w/v) bovine serum albumin at pH 8. Subsequent to incubation, mixtures are diluted with 1 ml of ice-cold buffer and centrifuged (10,000 g) for 5 min at 4° C. The supernatant will then be removed by aspiration, and the membrane pellet counted for adioactivity. Data is corrected for nonspecific binding (amount of radioactivity remaining membrane associated in the presence of 1 μM human insulin. In all assays the percentage of tracer bound in the absence of competing ligand was less than 15% to avoid ligand-depletion artifacts. A corresponding microtiter plate antibody assay using the IGF Type I receptor was employed to assess cross-binding to this homologous receptor.

X-Ray Crystallography.

Crystals of an analogue of human insulin containing histidines at positions A4 and A8 were grown by hanging-drop vapor diffusion in the presence of a 1:1.7 ratio of $Zn^{2+}$ to protein monomer and a 3.5:1 ratio of phenol to protein monomer in Tris-HCl buffer as known in the art. Drops consisted of 1 µl of protein solution (8 mg/ml in 0.02 M HCl) mixed with 1 of reservoir solution (0.38 M Tris-HCl, 0.1 M sodium citrate, 9% acetone, 4.83 mM phenol, and 0.8 mM zinc acetate at pH 8.4). Each drop was suspended over 1 ml of reservoir solution. Crystals (space group R3) were obtained at room temperature after two weeks. Data were collected from single crystals mounted in a rayon loop and flash frozen to 100° K. Reflections from 32.05-1.90 Å were measured with a CCD detector system on synchrotron radiation in Berkeley National Laboratory. Data were processed with programs DTREK. The crystal belongs to space group R3 with unit cell parameters: $a=b=78.09$ Å, $c=36.40$ Å, $\alpha=\beta=90°, \gamma=120°$. The structure was determined by molecular replacement using the computer program CNS. Accordingly, a model was obtained using the native TR dimer (Protein Databank (PDB) identifier 1RWE following removal of all water molecules, zinc- and chloride ions). A translation-function search was performed using coordinates from the best solution for the rotation function following analysis of data between 15.0 and 4.0 Åresolutions. Rigid-body refinement using CNS, employing overall anisotropic temperature factors and bulk-solvent correction, yielded values of 0.325 and 0.344 for R and $R_{free}$, respectively, for data between 19.2 and 3.0 Åresolution. Between refinement cycles, $2F_o-F_c$ and $F_o-F_c$ maps were calculated using data to 3.0 Åresolution; zinc and chloride ions and phenol molecules were built into the structure using the program O. Water molecules were calculated and checked using DDQ program. The geometry was continually monitored with PROCHECK; zinc ions and water molecules were built into the difference map as the refinement proceeded. Calculation of omit maps (especially in the first eight residues of B chain N terminus of each monomer) and further refinement were carried out using CNS, which implement maximum-likelihood torsion-angle dynamics and conjugate-gradient refinement.

Figure 3A:
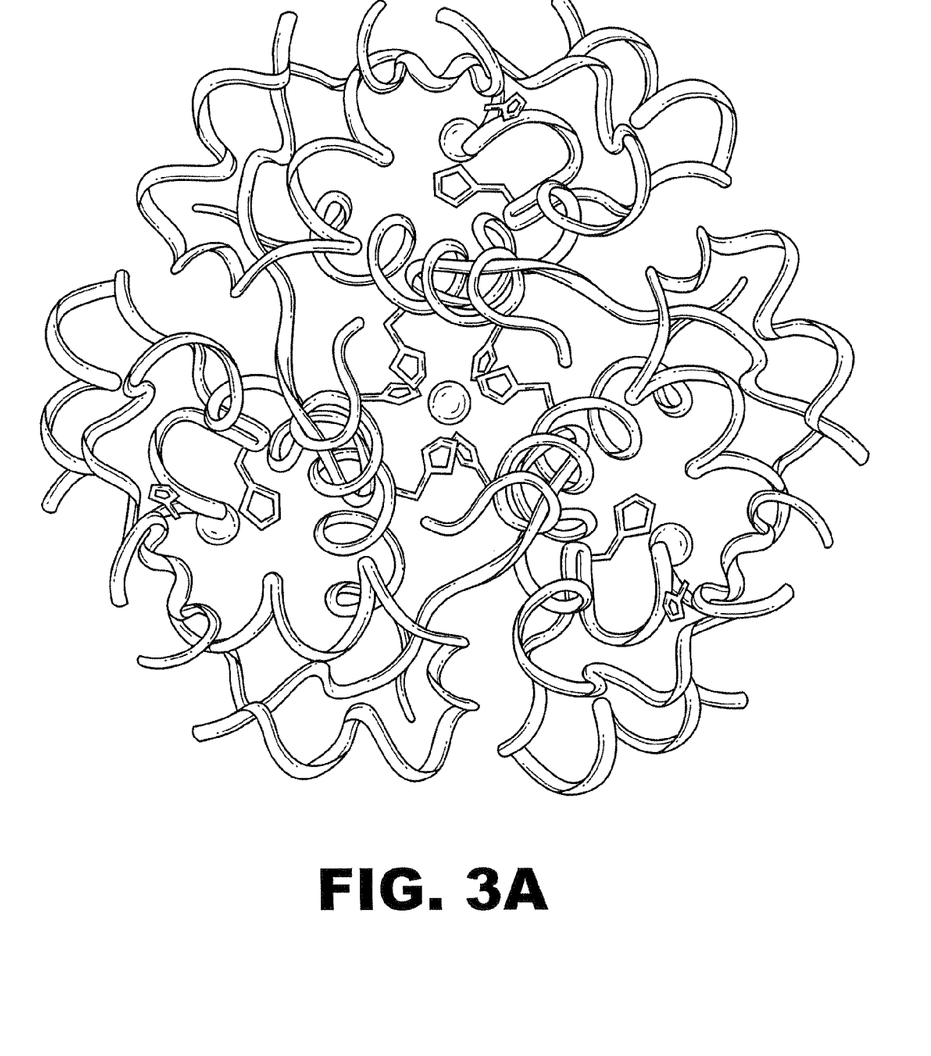
FIG. 3A is a representation of a variant $T_3R_3^f$ zinc hexamer. The side chains of $His^{A4,A8}$ and $His^{B10}$ in a $Zn^{2+}$-coordination site are shown.
Figure 3B:
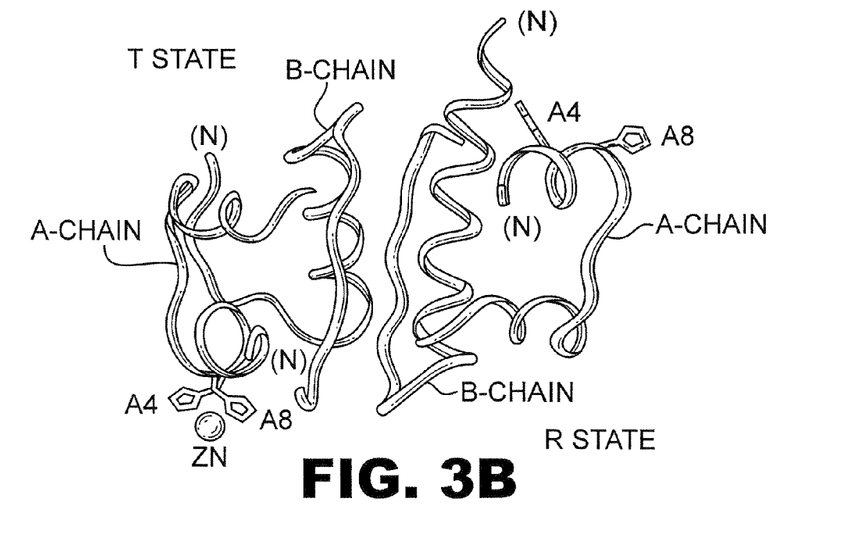
FIG. 3B is a ribbon representation of a crystal structure of a $His^{A4,A8}$ dimer. Ribbon representation of crystal structure of $His^{A4,A8}$-insulin. The A-chain of molecule 1 and 2 are shown in black and B-chain and B-chain N-terminal (B1-B8) α-helix in gray, residues of $His^{A4,A8}$ side chains are shown in black stick, and a $Zn^{2+}$-coordination site is noted.
Figure 3C:
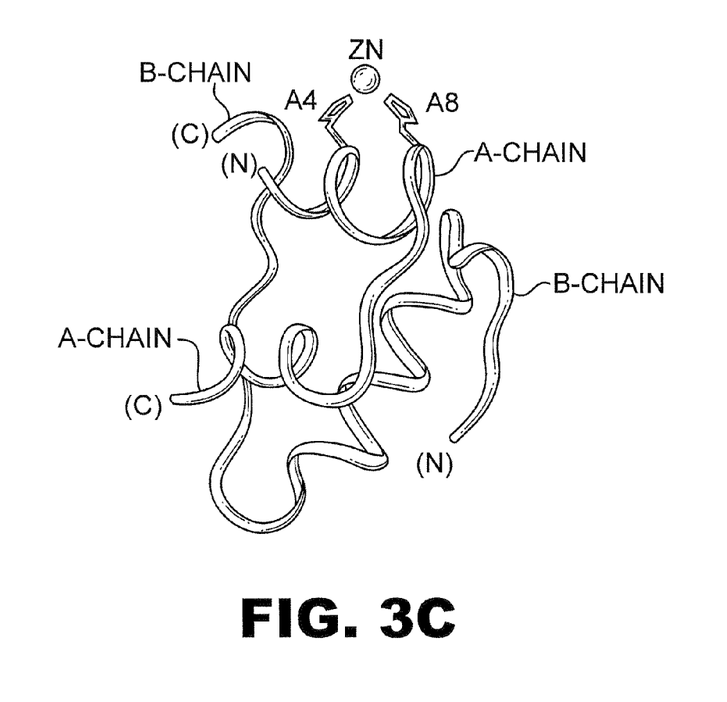
FIG. 3C is a representation of a crystal structure of $His^{A4,A8}$ monomer.
Figure 3D:
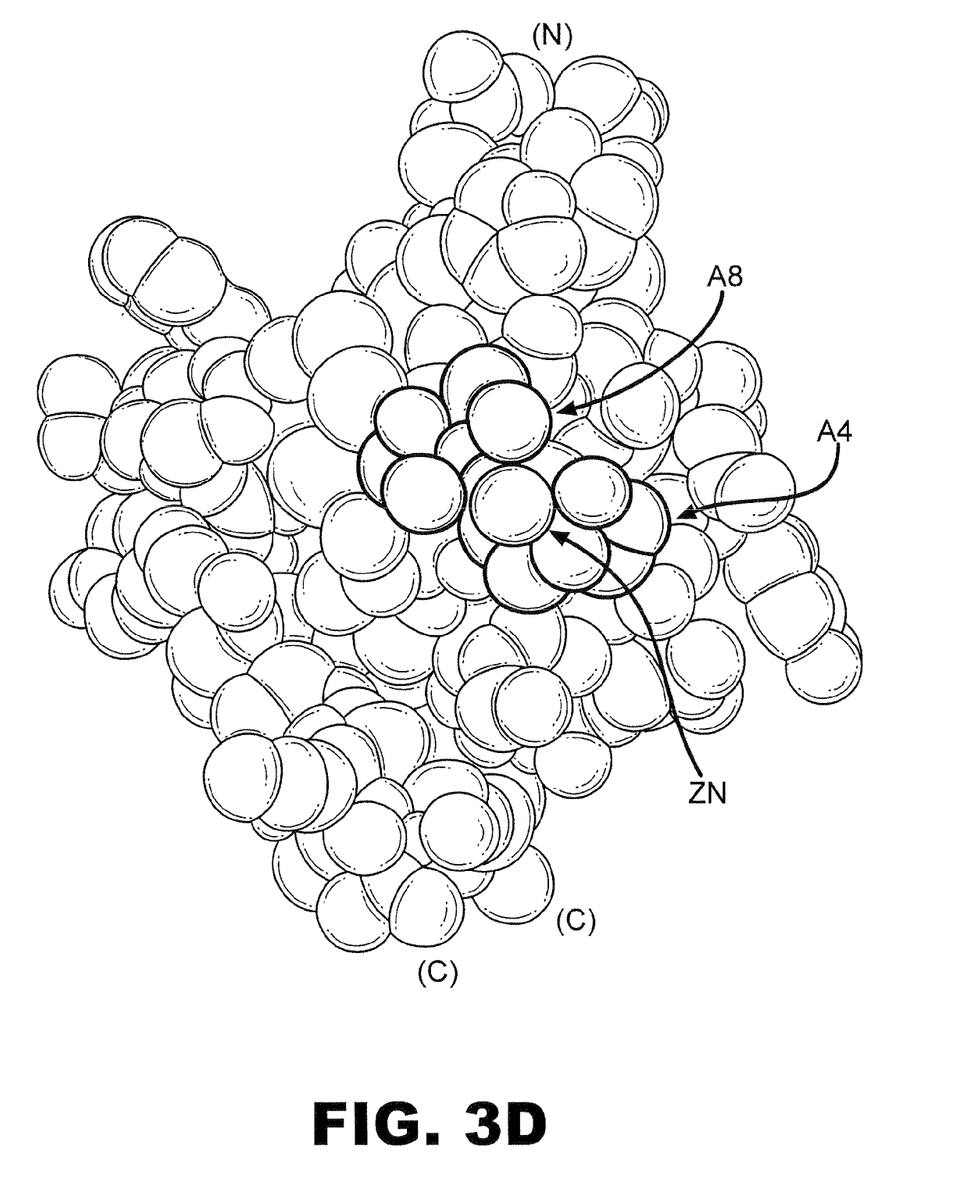
FIG. 3D is a space-filling representation of T-state promoter showing $His^{A4,A8}$ relation to classical the surface. The side chains of $His^{A4,A8}$ are shown in black with a $Zn^{2+}$-coordination site between the two His residues.

The crystal structure of [$His^{A4}$, $His^{A8}$]-insulin as a $T_3R_3^f$ zinc hexamer (FIG. 3A), determined to a resolution of 1.9 Å, contains five bound zinc ions instead of the two bound zinc ions that are ordinarily observed in wild-type crystal structures obtained under these conditions. Three novel zinc ions are observed coordinated by the side chains of histidines side chains at positions A4 and A8 in the three T-state protomers in addition to the two classical axial zinc ions coordinated by the wild-type histidine side chain at position B10.

Activities of the insulin analogues [$His^{A4}$, $His^{A8}$]-insulin, [$His^{A4}$, $His^{A8}$]-DKP-insulin, $His^{B1}$-insulin, $His^{B1}$-DKP-insulin, and $His^{A8}$-DKP-insulin relative to human insulin, whose affinity is 0.05 nM under assay conditions are provided in Table 1. For comparison purposes, the activity of DKP-insulin is also provided. Histidine substitutions at positions B1, A4, A8, or jointly at positions A4 and A8, do not significantly enhance cross-binding of these analogues to the IGF-I Type I receptor; any such increase is less than twofold (i.e., the level of increased cross-binding exhibited by the insulin analogue sold under the trademark HUMALOG®).

TABLE I

Affinity of Insulin and Insulin Analogues to Insulin Receptor

| Sample: | Affinity (relative to human insulin): |
|---|---|
| Human insulin | 100% |
| DKP-insulin | 161 ± 19 |
| $His^{A8}$-DKP-insulin | 167 ± 21 |
| [$His^{A4}$, $His^{A8}$]-insulin | 108 ± 4 |
| [$His^{A4}$, $His^{A8}$]-DKP-insulin | 201 ± 14 |
| $His^{B1}$-insulin | >180 |
| $His^{B1}$-DKP-insulin | 311 ± 48 |

These data indicate that the affinity of the analogues to the human insulin receptor is as great or greater than that of wild-type human insulin.

Circular Dichroism—Samples were dissolved in either 10 mM phosphate and 100 mM KCl (pH 7.4) or 0.01 N HCl (pH 2.0) at a protein concentration of 25 µM. To remove particulate matter and protein aggregates, samples were filtered (0.22 µM; Satorius, Goetlingen, Germany). Spectra, acquired with an Aviv spectropolarimeter (Aviv Biomedical, Inc., Lakewood, N.J.), were normalized. Data were obtained at 4° C. and fitted by non-linear least squares to a two-state model. CD Spectra for analogues were similar to native and DKP insulins (data not shown).

Fibrillation Assay—DKP-insulin and analogues were made 100 µM in a deoxygenated buffer consisting of 10 mM Tris-HCl (pH 7.4), 140 mM NaCl, with or without 1 mM $ZnCl_2$. Samples (in triplicate) were placed in sealed glass vials and placed on an automated tilting table at 37° C. At successive times aliquots were withdrawn and analyzed by a thioflavin T (ThT) fluorescence assay to determine the onset of fibrillation.

Fluorescence Spectroscopy—Thioflavin T (ThT) was made 1 mM in double-distilled water and stored at 4° C. in the dark. To monitor fibrillation, 10-µl aliquots obtained at indicated time points were mixed with 3 ml of ThT assay buffer (5 µM ThT in 50 mM Tris-HCl (pH 7.5) and 100 mM NaCl). Fluorescence measurements were performed using an Aviv spectrofluorometer in 1-cm quartz cuvettes. Emission spectra were collected from 470 to 500 nm following excitation at 450 nm; the integration time was 1 s. ThT in buffer without protein was used as baseline. The fibrillation lag time is defined as the time required to observe 2-fold enhancement in ThT emission. The threshold of 2-fold-enhanced ThT fluorescence is followed a rapid increase in turbidity associated with elongation of mature fibrils and a further increase in ThT fluorescence. Under these conditions, human insulin undergoes fibrillation in 3-4 days in the absence of zinc. Lag times prior to fibrillation of the analogues are provided in Table II.

TABLE II

Fibrillation Lag Times of DKP-insulin and analogues ± Zinc

| Sample (without Zn) | Lag time (days) | Sample (with Zn) | Lag time (days) |
|---|---|---|---|
| DKP-insulin | 7.7 ± 0.6 | DKP-insulin | 11.7 ± 2.5 |
| [$His^{A4}$, $His^{A8}$]-DKP-insulin | 22.7 ± 1.5 | [$His^{A4}$, $His^{A8}$]-DKP-insulin | >92 |
| $His^{B1}$-DKP-insulin | 6.8 ± 0.8 | $His^{B1}$-DKP-insulin | 20.3 ± 2.1 |
| $His^{A8}$-DKP-insulin | 21.3 ± 1.2 | $His^{A8}$-DKP-insulin | 34 ± 1.7 |

In the presence of zinc, each of the DKP analogues provides a greater fibrillation lag time than DKP insulin. The protective effect against fibrillation was especially pronounced for the DKP-insulin analogue carrying the His[44], His[48] substitutions in zinc. In the absence of zinc ions in a buffer consisting of 10 mM potassium phosphate and 140 mM KCl at pH 7.4 a single histidines substitution at position A8 increased the lag time prior to fibrillation from 3.5±0.9 days to 13±2.6 days at 37° C.

Based upon the foregoing disclosure, it should now be apparent that the polypeptide analogues provided herein will provide increased resistance to fibrillation while maintaining at least the majority of the activity of the polypeptide. The histidine substitutions specified herein may be employed to enhance the resistance of wild-type human insulin or to compensate for otherwise destabilizing effects of unrelated substitutions in the A- or B-chains. It is, therefore, to be understood that any variations evident fall within the scope of the claimed invention and thus, the selection of specific component elements can be determined without departing from the spirit of the invention herein disclosed and described.

I claim:

1. An isolated vertebrate insulin molecule comprising a polypeptide having an amino acid sequence containing one or more substitutions selected from at least one of:
   histidine residue substitutions at residues A4 and A8 relative to human insulin together; and
   a histidine residue substitution at residue B1 relative to human insulin.

2. The isolated vertebrate insulin molecule of claim 1, wherein the vertebrate insulin is a mammalian insulin.

3. The mammalian insulin of claim 2, wherein the mammalian insulin is human, porcine, bovine or equine insulin, and analogues thereof that additionally contain three or fewer additional conservative amino acid substitutions, and physiologically acceptable salts thereof.

4. The mammalian insulin of claim 3, wherein the A chain has a sequence of SEQ ID NO: 2.

5. The mammalian insulin of claim 2, comprising SEQ ID NO: 2.

6. The mammalian insulin of claim 5, wherein the B chain has a sequence selected from the group consisting of SEQ ID NOS: 3-8.

7. The mammalian insulin of claim 2, comprising SEQ ID NO: 10.

8. The mammalian insulin of claim 7, additionally comprising the SEQ ID NO: 2.

9. A pharmaceutical composition comprising a polypeptide according to claim 1.

10. The pharmaceutical composition of claim 9 additionally comprising zinc.

11. The pharmaceutical composition of claim 10, comprising about 2.2 to about 3.0 moles of zinc per mole of polypeptide.

12. A method of reducing blood glucose levels of a patient comprising administering a physiologically effective amount of the pharmaceutical composition of claim 9.

13. A nucleic acid comprising a sequence that encodes a polypeptide selected from the group consisting of an insulin A chain polypeptide containing histidine residue substitutions at residues A4 and A8 relative to human insulin, an insulin B chain polypeptide containing a histidine residue substitution at residue B1 relative to human insulin, and combinations thereof.

14. The nucleic acid of claim 13, additionally comprising a nucleic acid sequence encoding between 0 and about 34 amino acids between the A chain insulin sequence and the B chain insulin sequence.

15. An expression vector comprising the nucleic acid of claim 13.

16. A host cell transformed with the expression vector of claim 15.

17. A polypeptide comprising an insulin analogue or pro-insulin analogue having the amino acid sequence represented by formula I, (I)
R1-Val-Asn-Gln-His-Leu-Cys-Gly-Ser-His-Leu-Val- Glu-Ala-Leu-Tyr-Leu-Val-Cys-Gly-Glu-Arg-Gly-Phe- -continued
Phe-Tyr-Thr-R2-R3-Thr-Xaa$_{0-35}$-Gly-Ile-Val-R4-Gln- Cys-Cys-R5-Ser-Ile-Cys-Ser-Leu-Tyr-Gln-Leu-Glu- Asn-Tyr-Cys-Asn;

wherein R1 is His or Phe; wherein R2 is Pro, Lys, or Asp; wherein R3 is Lys or Pro; wherein R4 is His or Glu; wherein R5 is His or Thr; and wherein Xaa$_{0-35}$ is 0-35 of any amino acid or a break in the amino acid chain;
and further wherein at least one substitution selected from the group of the following amino acid substitutions is present:
R1 is His; and
R4 and R5 together are His.

18. The polypeptide of claim 17 comprising an amino acid sequence selected from the group consisting of SEQ ID NO: 2, and 4-8.

19. A vertebrate insulin comprising SEQ ID NO: 2 and additionally comprising a substitution of the B-chain selected from the group consisting of mutations at B28 and mutations at B29 relative to human insulin.

* * * * *

UNITED STATES PATENT AND TRADEMARK OFFICE
CERTIFICATE OF CORRECTION

PATENT NO.       : 8,343,914 B2
APPLICATION NO.  : 12/160187
DATED            : January 1, 2013
INVENTOR(S)      : Michael Weiss Page 1 of 1

It is certified that error appears in the above-identified patent and that said Letters Patent is hereby corrected as shown below:

In the Specification

Column 2; Line 20: "stifling" should be changed to --stirring--

Column 5; Line 52: "a His $^{A4,A8}$ dimer" should be changed to --a His $^{A4,A8}$ insulin dimer--

Signed and Sealed this
Fourth Day of June, 2013

Teresa Stanek Rea
*Acting Director of the United States Patent and Trademark Office*

```
                       SEQUENCE LISTING

<160> NUMBER OF SEQ ID NOS: 11

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 21
<212> TYPE: PRT
<213> ORGANISM: Homo sapiens

<400> SEQUENCE: 2

Gly Ile Val His Gln Cys Cys His Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Homo sapiens

<400> SEQUENCE: 4

His Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 5
<211> LENGTH: 30
<212> TYPE: PRT
<213> ORGANISM: Homo sapiens

<400> SEQUENCE: 5
```

His Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 6
<211> LENGTH: 30
<212> TYPE: PRT
<213> ORGANISM: Homo sapiens

<400> SEQUENCE: 6

His Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 7
<211> LENGTH: 30
<212> TYPE: PRT
<213> ORGANISM: Homo sapiens

<400> SEQUENCE: 7

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 8
<211> LENGTH: 30
<212> TYPE: PRT
<213> ORGANISM: Homo sapiens

<400> SEQUENCE: 8

His Val Asn Gln His Leu Cys Gly Ser Asp Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 9
<211> LENGTH: 21
<212> TYPE: PRT
<213> ORGANISM: Homo sapiens

<400> SEQUENCE: 9

Gly Ile Val Glu Gln Cys Cys His Ser Ile Cys Ser Leu Tyr Gln Leu
1               5                   10                  15

Glu Asn Tyr Cys Asn
            20

<210> SEQ ID NO 10
<211> LENGTH: 30
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa is Pro, Lys, Asp
<220> FEATURE:
<221> NAME/KEY: MISC_FEATURE
<222> LOCATION: (29)..(29)
<223> OTHER INFORMATION: Xaa is Lys or Pro

<400> SEQUENCE: 10

His Val Asn Gln His Leu Cys Gly Ser His Leu Val Glu Ala Leu Tyr
1               5                   10                  15

```
Leu Val Cys Gly Glu Arg Gly Phe Phe Tyr Thr Xaa Xaa Thr
            20                  25                  30
```

```
<210> SEQ ID NO 11
<211> LENGTH: 86
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is His or Phe
<220> FEATURE:
<221> NAME/KEY: MISC_FEATURE
<222> LOCATION: (28)..(28)
<223> OTHER INFORMATION: Xaa is Pro, Lys or Asp
<220> FEATURE:
<221> NAME/KEY: MISC_FEATURE
<222> LOCATION: (29)..(29)
<223> OTHER INFORMATION: Xaa is Lys or Pro
<220> FEATURE:
<221> NAME/KEY: MISC_FEATURE
<222> LOCATION: (31)..(65)
<223> OTHER INFORMATION: x is 0 - 35 of any naturally occurring amino
      acid
<220> FEATURE:
<221> NAME/KEY: MISC_FEATURE
<222> LOCATION: (69)..(69)
<223> OTHER INFORMATION: Xaa is His or Glu
<220> FEATURE:
<221> NAME/KEY: MISC_FEATURE
<222> LOCATION: (73)..(73)
<223> OTHER INFORMATION: Xaa is His or Thr

<400> SEQUENCE: 11

Xaa Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Thr Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Gly Ile Val Xaa Gln Cys Cys Xaa Ser Ile Cys Ser Leu Tyr Gln
65                  70                  75                  80

Leu Glu Asn Tyr Cys Asn
                85
```